United States Patent
Prindle et al.

(10) Patent No.: US 8,163,123 B2
(45) Date of Patent: Apr. 24, 2012

(54) BIFURCATION CATHETER DUAL BALLOON BOND AND METHODS

(75) Inventors: Katherine Prindle, Robbinsdale, MN (US); Karen Turner, Lino Lakes, MN (US); Mary Bronson, Elk River, MN (US); Matt Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 878 days.

(21) Appl. No.: 12/183,869

(22) Filed: Jul. 31, 2008

(65) Prior Publication Data

US 2010/0030316 A1 Feb. 4, 2010

(51) Int. Cl.
*B32B 37/06* (2006.01)
(52) U.S. Cl. .................................. 156/272.8
(58) Field of Classification Search .............. 156/272.2, 156/272.8
See application file for complete search history.

(56) References Cited

U.S. PATENT DOCUMENTS

| | | | |
|---|---|---|---|
| 6,210,429 B1 | 4/2001 | Vardi et al. | |
| 6,325,826 B1 | 12/2001 | Vardi et al. | |
| 6,409,863 B1 * | 6/2002 | Williams et al. | 156/198 |
| 6,692,483 B2 | 2/2004 | Vardi et al. | |
| 6,706,062 B2 | 3/2004 | Vardi et al. | |
| 7,220,275 B2 | 5/2007 | Davidson et al. | |
| 2004/0176837 A1 * | 9/2004 | Atladottir et al. | 623/1.35 |
| 2005/0015108 A1 * | 1/2005 | Williams et al. | 606/194 |
| 2005/0102019 A1 | 5/2005 | Yadin | |
| 2006/0135909 A1 | 6/2006 | Holman et al. | |
| 2007/0203562 A1 | 8/2007 | Malewicz et al. | |

FOREIGN PATENT DOCUMENTS

WO 2009088953 7/2009

* cited by examiner

*Primary Examiner* — Richard Crispino
*Assistant Examiner* — Daniel McNally
(74) *Attorney, Agent, or Firm* — Seager, Tufte & Wickhem, LLC

(57) ABSTRACT

A catheter assembly includes a main catheter branch having a catheter shaft and a distal end portion. A main balloon and a side balloon are positioned at the distal end portion of the catheter shaft. The main balloon includes a distal waist portion at a distal end thereof and a proximal waist portion at a proximal end thereof. The side balloon includes an inflatable portion, a proximal waist portion, and a distal waist portion, wherein the proximal and distal waist portions define a side inflation lumen. The proximal waist portion of the side balloon and the proximal waist portion of the main balloon are secured to the distal end portion of the catheter shaft at a single bond or connection point to create a proximal balloon joint, wherein the main inflation lumen is in fluid communication with the main balloon and the side inflation lumen.

6 Claims, 6 Drawing Sheets

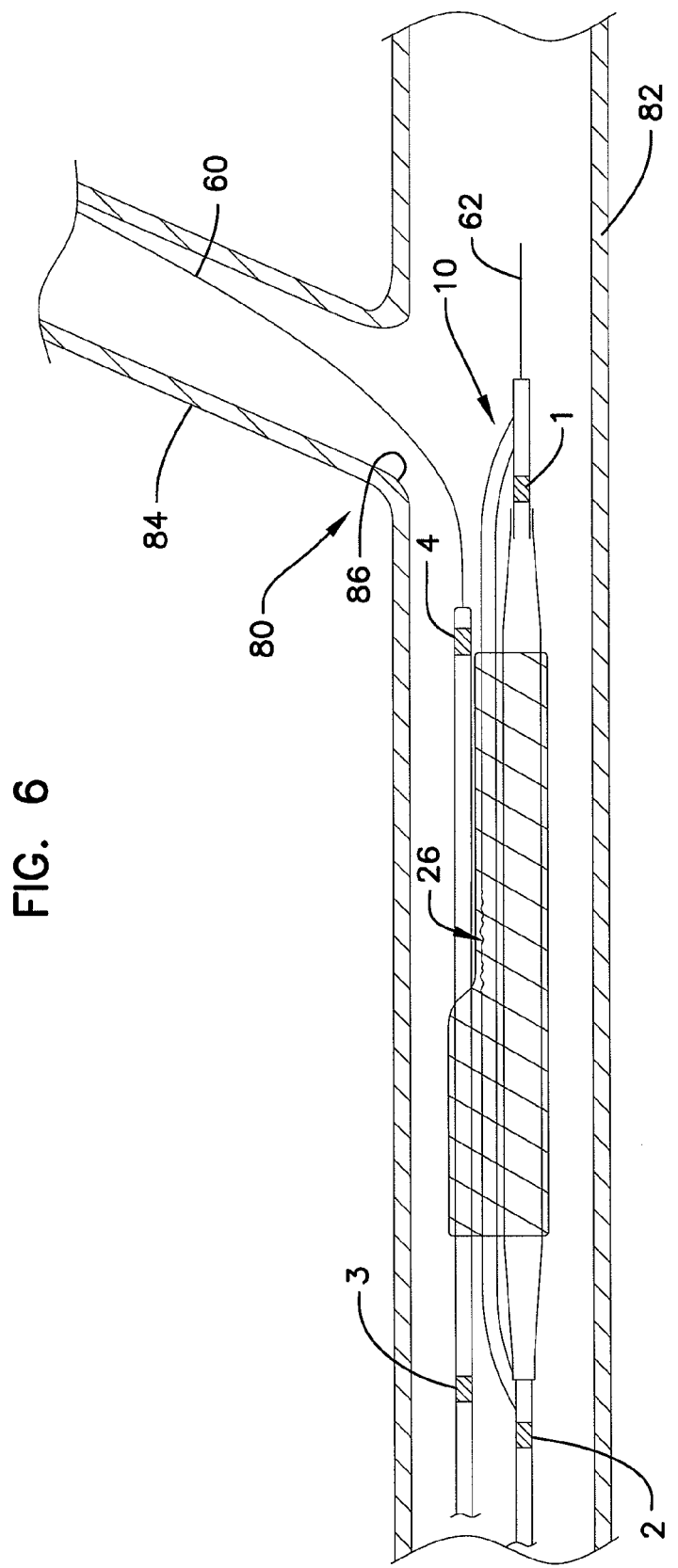

BIFURCATION CATHETER DUAL BALLOON BOND AND METHODS

TECHNICAL FIELD

This disclosure relates to catheter systems and methods for treating vessel bifurcations. This disclosure more particularly relates to balloon bonding arrangements for bifurcation catheter systems.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY

The present disclosure relates generally to catheter assemblies for treatment of bifurcated lumens in a patient, such as vessel bifurcations. In one example, the catheter assembly includes a main catheter branch and a side catheter branch. The main catheter branch includes a catheter shaft having a distal end portion. The catheter shaft defines a main inflation lumen. A main balloon and a side balloon are positioned at the distal end portion of the catheter shaft and in fluid communication with the main inflation lumen. The main balloon includes a distal waist portion at a distal end thereof, and a proximal waist portion at a proximal end thereof. The side balloon includes an inflatable portion, a proximal waist portion, and a distal waist portion, wherein the proximal and distal waist portions define a side inflation lumen. The inflatable portion of the side balloon is configured to extend radially outward relative to the main balloon when the side balloon is inflated. The proximal waist portion of the side balloon and the proximal waist portion of the main balloon are secured to the distal end portion of the catheter shaft at a single bond to create a proximal balloon joint, wherein the main inflation lumen is in fluid communication with the main balloon and the side inflation lumen.

There is no requirement that an arrangement or method include all features characterized herein to obtain some advantage according to this disclosure.

DESCRIPTION OF THE DRAWINGS

FIG. 6 is a schematic side view of the catheter assembly shown in FIG. 1 in a position prepared for treatment of a vessel bifurcation.

DETAILED DESCRIPTION

I. Background

Figure 1:
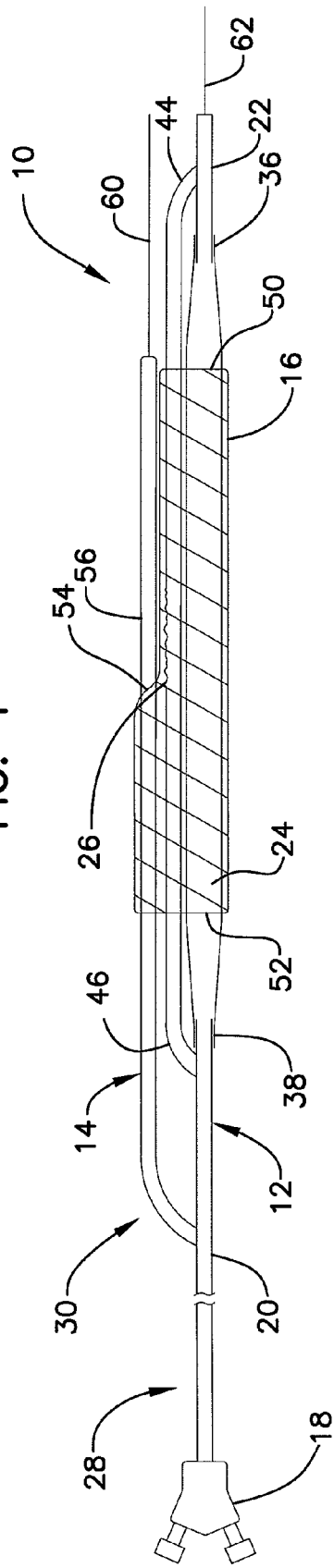
FIG. 1 is a schematic representation of an exemplary catheter assembly for treatment of a vessel bifurcation, the assembly constructed having a proximal end portion and distal end portion, wherein the distal end portion includes main and side balloons and main and side catheter branches.
Figure 2:
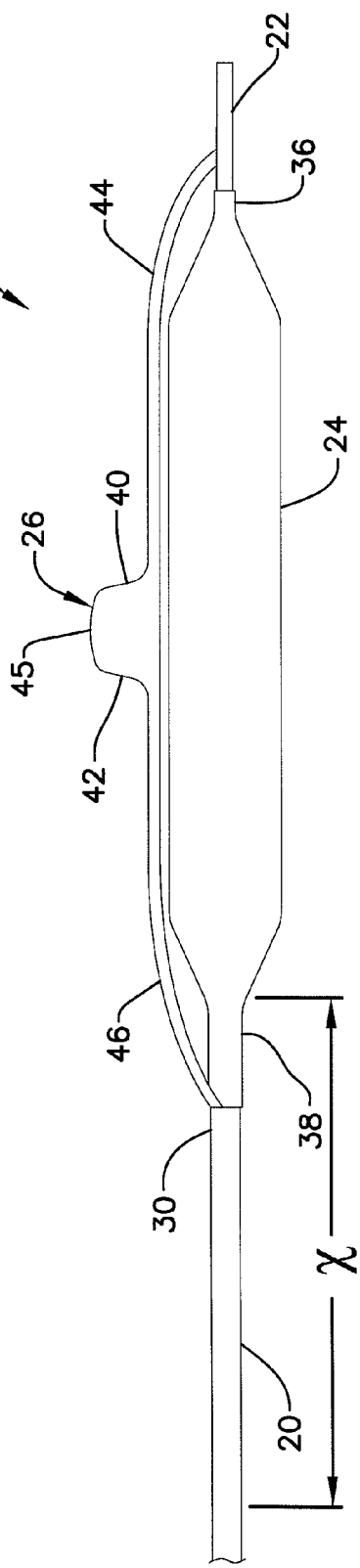
FIG. 2 is a schematic side view of the distal end portion of the catheter assembly shown in FIG. 1 with the stent and side catheter branch removed for clarity.

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The example catheter assemblies disclosed herein include at a distal end portion thereof a main catheter branch and a side catheter branch. The side catheter branch typically includes a side guidewire housing that defines a side guidewire lumen. A distal end portion of the side catheter branch is configured to extend into a branch vessel at a vessel bifurcation. The side catheter branch is used to align features of a stent carried by the proximal end portion of the vessel bifurcation treatment system with an ostium (also referred to as a branch vessel opening) into the branch vessel.

The main catheter branch includes a catheter shaft having a distal end portion. A main balloon and a side balloon are positioned at the distal end portion of the catheter shaft. A main catheter branch includes a main guidewire housing that defines a main guidewire lumen. A distal waist portion of the main balloon is operably mounted to the main guidewire housing. A proximal waist portion of the main balloon is operably mounted to the distal end portion of the catheter shaft.

The side balloon is positioned on a side inflation member that extends generally in parallel with the main balloon. The side inflation member defines a side inflation lumen. The side inflation member includes proximal and distal segments that are connected in fluid communication with the side balloon. The distal and proximal segments of the side inflation member can alternatively be considered elongate waist portions of the side balloon that extend in the distal and proximal directions, respectively.

The waist portion of a balloon is typically at one of the opposing ends of the balloon. The waist portion is used to secure or otherwise mount the balloon to a mounting surface, such as the outer surface of a shaft. Some example mounting surfaces for the waist portions of a main balloon are the outer surface of a distal end portion of a catheter shaft and the outer surface of a main guidewire housing. The waist portion is typically configured not to expand in size when the balloon is inflated with inflation fluid. In many instances a balloon is formed by molding from a length of tubular structure (e.g., a catheter shaft comprising a thermoplastic polymeric material). The portions of the tubular structure extending on opposite sides of the molded balloon can be considered waist portions of the balloon regardless of the length of the waist portions.

Figure 9:
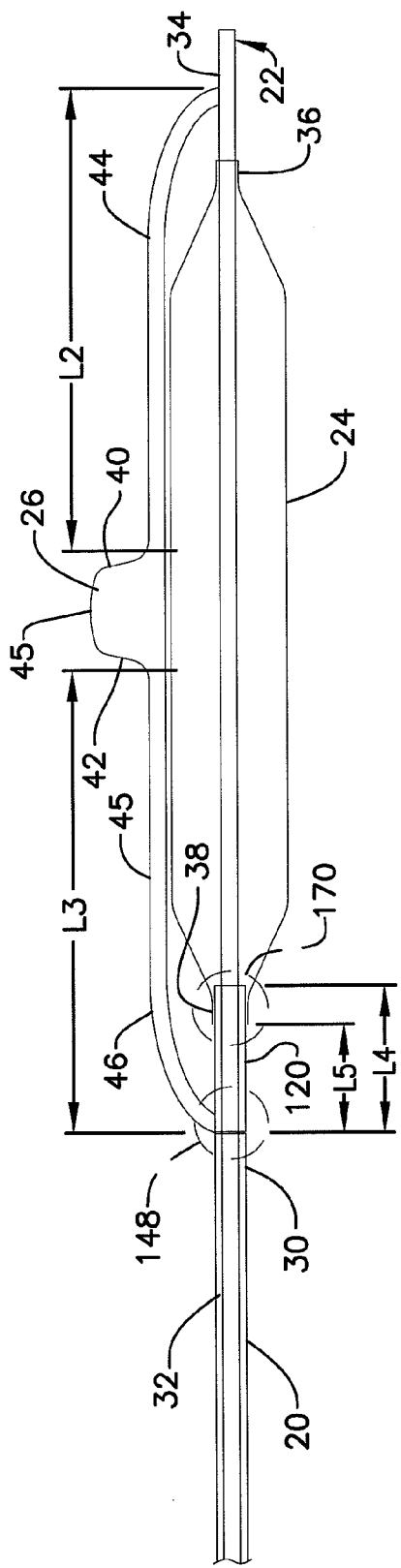
FIG. 9 is a schematic cross-sectional side view of another example catheter assembly having separate main balloon and side balloon joints.
Figure 11:
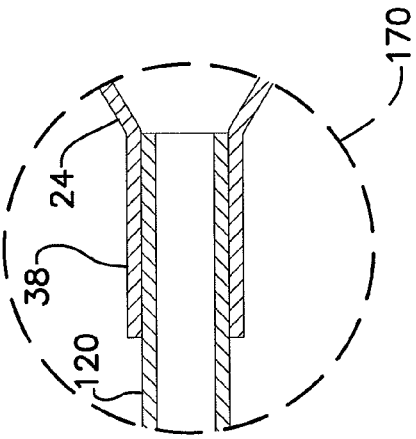
FIG. 11 is a schematic enlarged view of the main balloon joint shown in FIG. 9.
Figure 10:
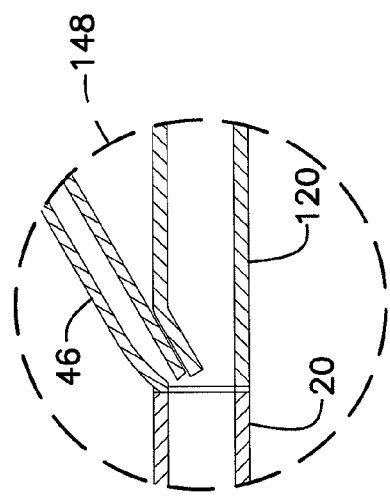
FIG. 10 is a schematic enlarged view of the side balloon joint shown in FIG. 9.

Referring now to FIGS. 9-11, an example distal end portion of a main catheter branch 112 is shown in cross-section. The main catheter branch 12 includes a catheter shaft 20 having a distal end portion 30 and a shaft distal segment 120 that together define a main inflation lumen 32. A main guidewire housing 32 extends beyond the distal end portion 30 of the catheter shaft. A main balloon 24 has a distal waist 36 at its distal end that is operably mounted to the main guidewire housing 32. A proximal waist 38 at a proximal end of the main balloon 24 is operably mounted to the shaft distal segment 120 at a main balloon proximal joint 170.

A side balloon 26 is positioned adjacent to the main balloon 24. The side balloon 26 includes an inflatable portion 45, a distal waist portion 44 extending from a distal side 40, and a proximal waist portion 46 extending from a proximal side 42. The inflatable portion 45 is positioned at a location between the distal and proximal waists 36, 38 of the main balloon. The waist portions 44, 46 define a side inflation lumen 45 that provides fluid communication from the main inflation lumen 32 to the side balloon 26. When inflated, the side balloon 26 extends radial outward relative to the main balloon 24 (i.e., a longitudinal axis of the main balloon 24). The distal and proximal waists 44, 46 can alternatively be referenced as distal and proximal segments of a side inflation member.

Typically, a distal end of the distal waist 44 is operably mounted to the main guidewire member 22 distal of the main balloon 24, and the proximal end of the distal waist 44 is operably mounted in fluid communication with the side balloon 26. A distal end of the proximal waist 46 is operably mounted in fluid communication to the side balloon 26, and a proximal end of the proximal waist 44 is operably mounted to the distal end portion of the catheter shaft 20 in fluid communication with the main inflation lumen 32 at a side balloon proximal joint 148. The side balloon proximal joint 148 is spaced from a distal end of the shaft distal segment 120 a distal L4, which is also the approximate length of shaft distal segment 120. The side balloon proximal joint 148 is also spaced from a distal end of the proximal waist 38 of the main balloon 24 a distance L5. The distance L4 is typically in the range of about 20 mm to about 50 mm.

A separate shaft distal segment 120 is typically used to provide a joint between the proximal end of the distal segment 120 and the distal end of the shaft 30 at which the proximal waist 46 of the side balloon can be secured in fluid communication with the main inflation lumen 32. In order to create fluid communication with the proximal waist 46, the three components (proximal waist 46, distal segment 120 and catheter shaft 20) are bonded together simultaneous using, for example, a heat bonding technique. Prior to the simultaneous bonding, a first mandrel is inserted from the catheter shaft 30 into the distal segment 120, and a second mandrel is inserted from the catheter shaft 30 into the proximal waist 46. In some arrangements, one or both of the catheter shaft 30 at a distal end thereof and distal segment 120 at a proximal end thereof has at least one slit formed therein to facilitate insertion of the second mandrel from catheter shaft 30 into the proximal waist 46 while maintaining alignment and contact between the catheter shaft 30 and the distal segment 120. In one bonding method, heat is then applied to the three components while the first and second mandrels are in place to bond the three components to each other in fluid communication. Other bonding techniques, such as adhesives and laser welding, can be used to bond the three components together. In separate bonding steps, the proximal waist 38 of the main balloon 24 is bonded to the distal segment 120.

The use of a separate side balloon proximal joint 148 at a location proximal of the main balloon proximal joint 170, and positioning the proximal joint 148 a distance L5 from the proximal end of the main balloon results in a number of potential disadvantages. For example, the use of two separate joints and a separate distal segment 120 of the catheter shaft proximal of the main balloon 24 can result in additional stiffness in the main catheter branch 112 that limits bending and rotation. Reducing flexibility at the distal end of the main catheter branch 112 can reduce incidence of self radial alignment of the side balloon and features of a stent (e.g., stent 16 shown in FIG. 1) carried by the main balloon 24 with an ostium of a branch vessel when treating a vessel bifurcation (e.g., vessel bifurcation 80 shown in FIGS. 6-8). Another example disadvantage relates to the processes and methods involved in manufacture of the main catheter branch 112. Formation of each of the joints 148, 170 requires time and additional steps. Each manufacturing step creates opportunity for errors and must be monitored for quality. Reducing the number of joints can reduce the overall time requirements for manufacture and the number of steps in the manufacturing process, which can result in reduced cost and improved consistency in manufacturing processes. Reducing the number of joints in this case can also eliminate an extra part from the assembly. If the side balloon proximal joint 148 is combined with the main balloon proximal joint 170 as will be described below, the distal segment 120 can be eliminated from the main catheter branch 112. Reducing the number of parts can reduce the cost of the assembly and reduce the complexity of the manufacturing process.

II. The Example Illustrated in FIGS. 1-5

Figure 3:
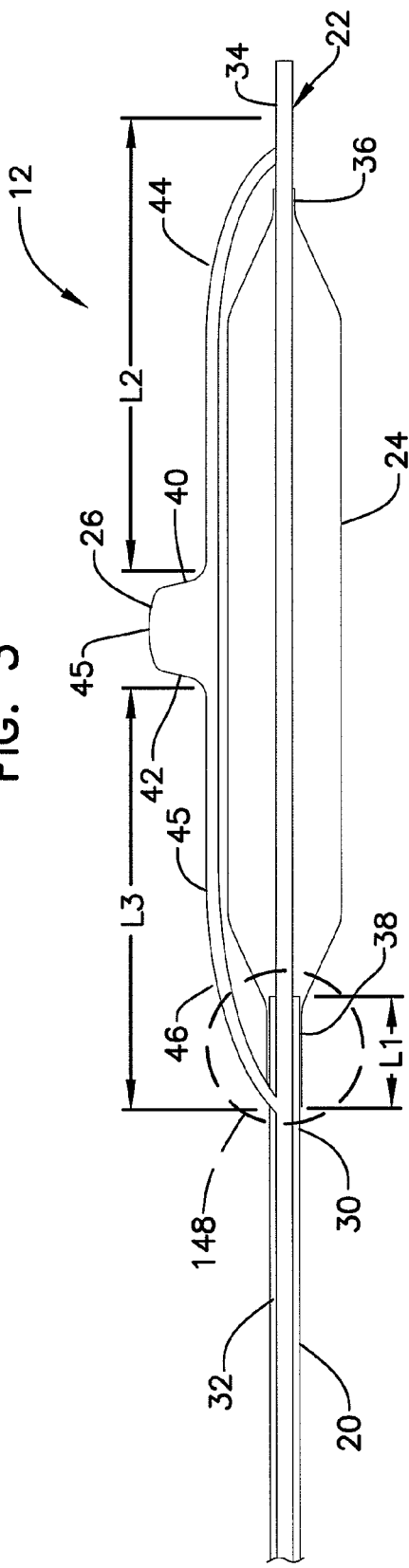
FIG. 3 is a schematic cross-sectional side view of the distal end portion of the catheter assembly shown in FIG. 2.
Figure 5:
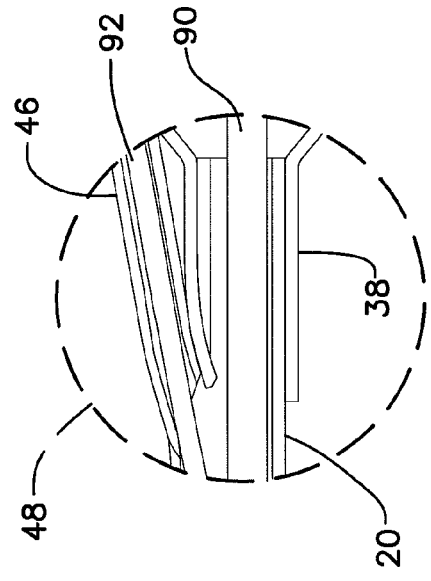
FIG. 5 is a schematic enlarged view of the dual balloon joint shown in FIG. 3 with mandrels inserted.
Figure 4:
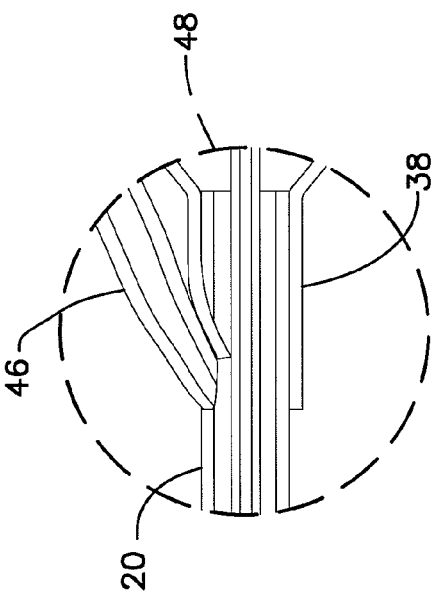
FIG. 4 is a schematic enlarged view of the dual balloon joint shown in FIG. 3.

An example catheter assembly 10 is shown schematically with reference to FIGS. 1-8. The catheter assembly 10 is configured for treatment of a vessel bifurcation such as the vessel bifurcation 80 shown in FIGS. 6-8. The catheter assembly 10 includes a main catheter branch 12, a side catheter branch 14, and a stent 16. The main catheter branch 12 includes a catheter shaft 20 having a proximal end portion 28 and a distal end portion 30. The catheter shaft 20 further defines a main inflation lumen 32 (see FIG. 3). The main catheter branch 12 further includes a main guidewire housing 22. The main guide wire housing 22 defines a main guidewire lumen 34 as shown in FIG. 3. The main catheter branch further includes a main balloon 24 extending along the guidewire housing 22. A proximal waist 38 of the main balloon 24 is operably mounted to the catheter shaft 20, and a distal waist of the main balloon 24 is operably mounted to the main guidewire housing 22.

The main catheter branch 12 further includes a side balloon 26. The side balloon 26 includes an inflatable portion 45, a waist 44, and proximal waist 46. The waist members 44, 46 define a side inflation lumen 45 through which inflation fluid is provided to the side balloon 26. The distal waist 44 has a length L2 in the range of about 3 to about 15 mm, and more preferably about 6 to about 10 mm. The proximal waist 46 has a length L2 in the range of about 3 to about 15 mm, and more preferably about 6 to about 10 mm. The side balloon includes front and rear sides 40, 42 from which the distal and proximal waists 44, 46 extend. When uninflated, the inflatable portion 45 of the side balloon 24 maintains a generally collapsed profile (e.g., see side balloon 24 in the collapsed state shown in FIGS. 1, 6 and 7). When inflated, the inflatable portion of the side balloon 26 extends radially outward relative to the longitudinal axis of the main balloon 24 (see FIGS. 2, 3 and 8).

Typically, a distal end of the distal waist 44 is operably mounted to the main guidewire member 22 distal of the main balloon 24. The proximal end of the distal waist 44 is operably mounted in fluid communication with the side balloon 26. A distal end of the proximal waist 46 is operably mounted in fluid communication to the side balloon 26. A proximal end of the proximal waist 44 is operably mounted to the distal end portion of the catheter shaft 20 in fluid communication with the main inflation lumen 32 at a proximal joint 48. The main balloon 24 is also coupled in fluid communication with the inflation lumen 32 at the proximal joint 48 via the proximal waist 38 of the main balloon 24. The proximal joint 48 is spaced from a distal end of the shaft distal segment 120 a distance L1. The distance L1 can be the approximate length of the proximal waist 38 of the main balloon 24. The distance L4 is typically in the range of about 1 mm to about 10 mm, and more preferably in the range of about 2 mm to about 5 mm.

In order to create fluid communication between the main inflation lumen 32 and side balloon 26, the proximal waist 46, distal portion 30 of the catheter shaft 20, and main balloon proximal waist 38 are bonded together simultaneously using, for example, a heat bonding technique. Prior to the bonding, a first mandrel 90 is inserted from the catheter shaft 30 into the side balloon proximal waist 46, and a second mandrel 92 is inserted from the catheter shaft 30 into the main balloon proximal waist 38 (see FIG. 5). In some arrangements, one or both of the catheter shaft 20 and main balloon proximal waist 38 has at least one slit formed therein to facilitate insertion of the second mandrel from catheter shaft 30 into the proximal waist 46. In one bonding method, heat is then applied to the proximal joint 48 while the first and second mandrels are in place. The applied heat bonds the catheter shaft 20, the side balloon proximal waist 46, and main balloon proximal waist 38 to each other in fluid communication.

Providing a proximal joint 48 wherein the side balloon 26 (via the proximal waist 46) and the main balloon 24 (via the proximal waist 38) are bonded together at a single joint in fluid communication with each other and the main inflation lumen 32 results in a number of potential advantages as compared to the two proximal joint configuration of the main catheter branch 112. For example, since bonding two or more members together (e.g., catheter shaft 20 with a balloon waist of balloon 24 or 26) typically results in a greater stiffness along the main catheter branch 12, the use of a single proximal joint to bond both balloons 24, 26 to the catheter shaft 20 can provide additional flexibility along the distal portion of the main catheter branch 112. Increasing flexibility at the distal portion of the main catheter branch 112 can improve the likelihood of self-radial alignment of the side balloon and features of the stent 16 carried by the main balloon 24 with an ostium of a branch vessel when treating a vessel bifurcation (e.g., vessel bifurcation 80 shown in FIGS. 6-8). As the catheter assembly 10 is advanced over guidewires (e.g., guidewires 60, 62 described below) to the vessel bifurcation treatment site, the distal end of the catheter assembly 10 can become immobile in the vessel due to, for example, interference of the assembly 10 with the vessel lumen or relative twist of the guidewires, which inhibits advancement of the assembly 10 or proper alignment with the ostium of the branch vessel. Providing some rotational and bending flexibility in the main catheter branch 12 at the distal end portion 30 proximal of the balloons 24, 26 can help the catheter assembly 10 become free from a bind and self-radially align with the branch vessel ostium.

Another example advantage of the single proximal joint arrangement of FIGS. 1-8 relates to the processes and methods involved in manufacture of the main catheter branch 12. Consolidating the proximal balloon joints to a single joint 48 can reduce the overall time requirements for manufacture and simplify the number of steps in the manufacturing process, which can results in reduced cost and improved consistency in manufacturing processes and quality. Reducing the number of proximal balloon joints can also eliminate an extra part from the assembly, such as the shaft distal segment 120. Reducing the number of parts can reduce the cost of the assembly and reduce the complexity of the manufacturing process.

The side balloon proximal waist 46 of the main catheter branch 12 has a shorter length extending proximal of a proximal end of the stent 16 as compared to the arrangement of main catheter branch 112. The shorted portion of the proximal waist 46 that extends proximal of the proximal end of the stent 16 in main catheter branch 12 is less susceptible to snagging or otherwise catching on objects prior to and during advancement of the main branch 12 through a body lumen to a bifurcation treatment site, and the subsequent removal of the main branch 12 from the body. Further, the shorter distance between the proximal joint 48 and the connection point of the distal waist 44 to the guidewire housing 22 distal of the main balloon reduces the likelihood of misalignment of the side balloon 26 with features of the stent (e.g., the stent lateral branch opening) and the ostium of a branch vessel prior to and during expansion of the stent 16 when treating the vessel bifurcation.

These and other advantages can results from the single proximal balloon joint or bond shown and described herein. The single proximal balloon joint or bond can also be referred to as a dual balloon bond, since it involves bonding two balloons (via balloon waists 38 and 46) in fluid communication with the main inflation lumen 32 at a single bond or joint location using a single bonding process.

III. The Example Vessel Bifurcation Treatment Illustrated in FIGS. 6-8

Figure 7:
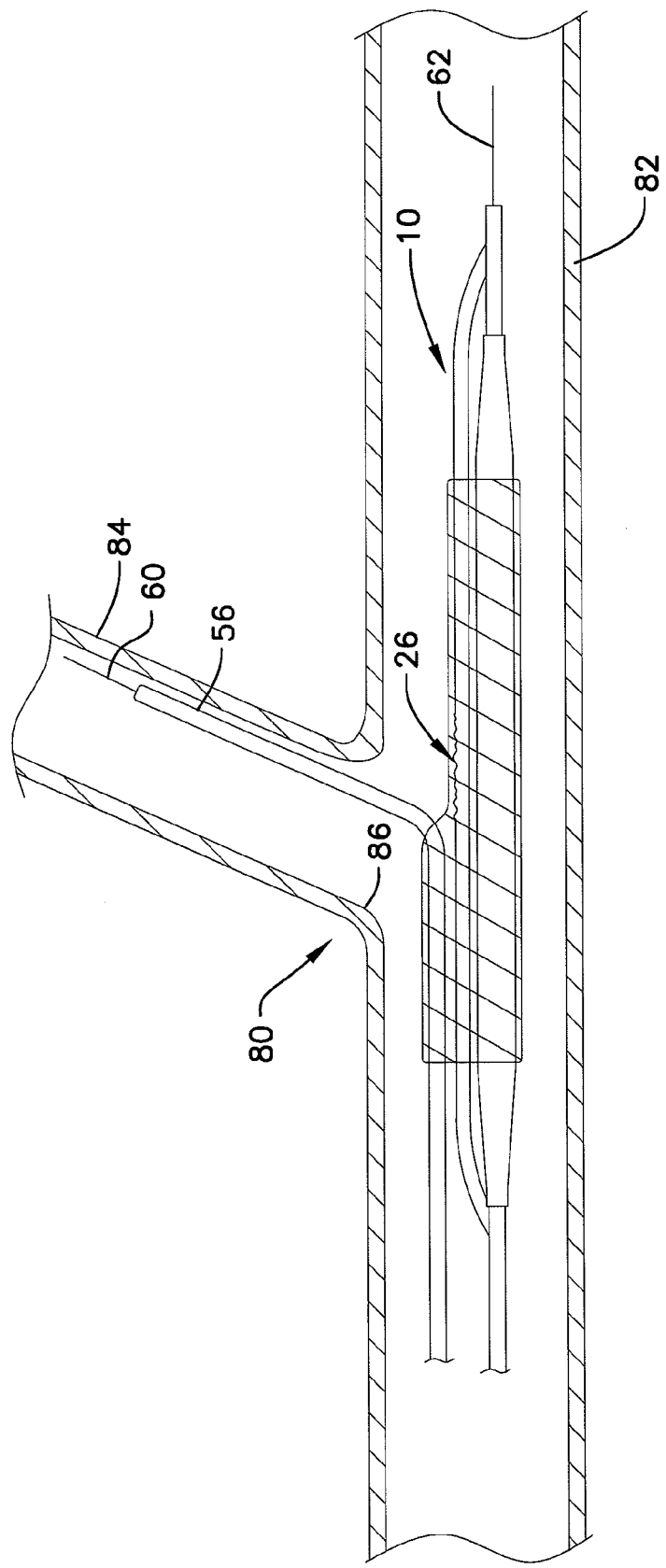
FIG. 7 is a schematic side view of the catheter assembly shown in FIG. 6 with the side catheter branch extending into a branch vessel of the vessel bifurcation.
Figure 8:
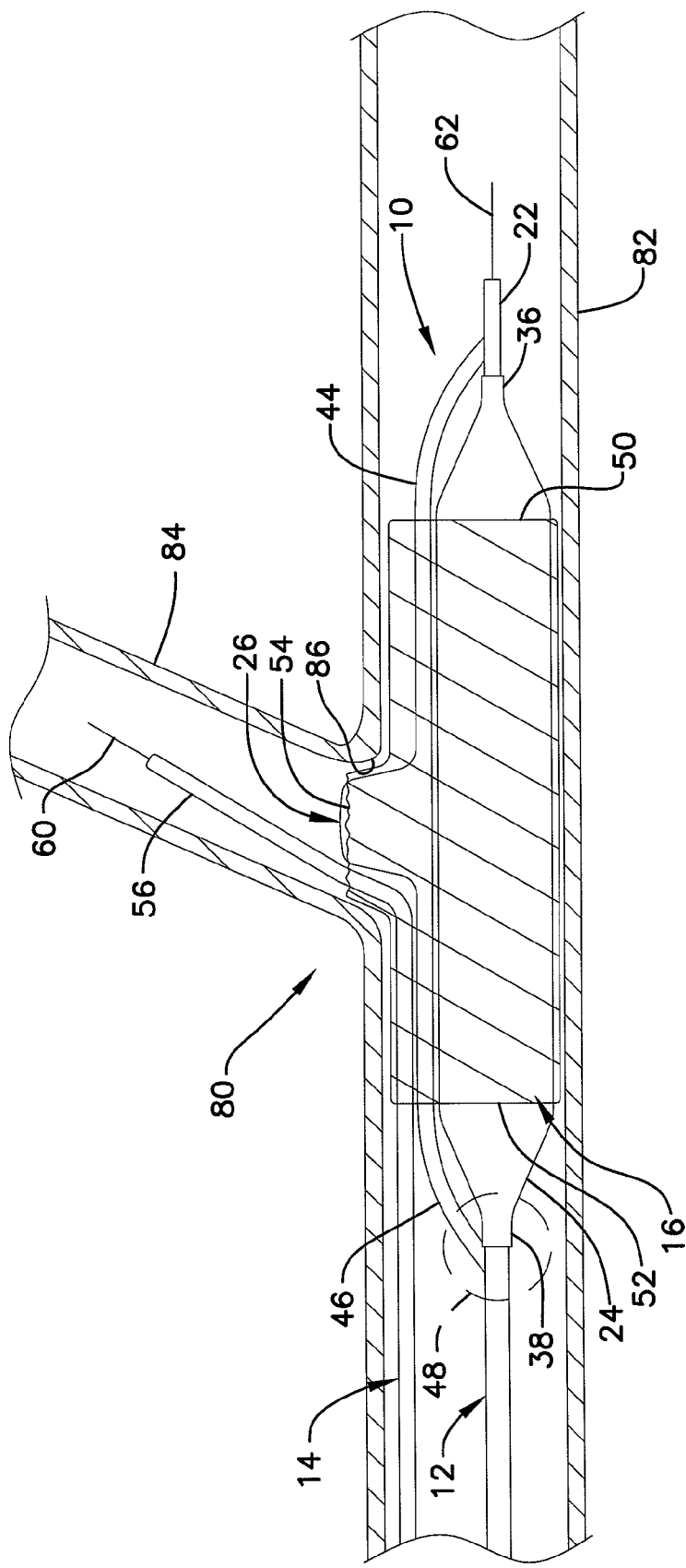
FIG. 8 is a schematic side view of the catheter assembly shown in FIG. 7 with the side and main balloons inflated and the stent expanded at the vessel bifurcation.

The catheter assembly 10 described above with reference to FIGS. 1-6 can be used for treatment of a vessel bifurcation 80 as shown in FIGS. 6-8. Typically, a main vessel guidewire 62 is inserted into a main vessel 82 of the vessel bifurcation 80 to a point distal of the vessel bifurcation. A branch vessel guidewire 60 is advanced to the vessel bifurcation and inserted through an ostium or opening 86 of a branch vessel 84. A proximal end of the main vessel guidewire 62 is then inserted into the main guidewire lumen 34, and a proximal end of the branch vessel guidewire 60 is inserted into a branch guidewire lumen defined by the side catheter branch 14. The catheter assembly 10 is advanced over the guidewires 60, 62 to the vessel bifurcation as shown in FIG. 6. The catheter assembly 10 is then advanced further distally until the distal end portion 56 of the side catheter branch 14 is positioned within the branch vessel 60. A marker system can be used to help confirm proper radial and axial alignment of the lateral branch opening 54 of the stent 16 relative to the ostium 86 into the branch vessel 84. An example four-marker system is described below.

As mentioned above, the increased flexibility of the distal portion of the main catheter branch 12 resulting from the single proximal balloon bond 48 can promote improved self-radial alignment of the side balloon 26 and lateral branch opening 54 of the stent 16 relative to the ostium 86. The single proximal balloon bond 48, which is positioned at the distal most location along the catheter shaft 20, provides for maximum twist per unit length in the area X at the distal end portion 30 (see FIG. 2), wherein the area X represents the area in which the two proximal balloon bonds of main catheter branch 112 typically exist.

After proper positioning of the catheter assembly 10 is confirmed, the main and branch balloons 24, 26 are inflated. Typically, inflation of the side balloon 26 can also result in expansion of expandable structure 55 surrounding the lateral branch opening 54. The expanded expandable structure 55 can extend through the ostium 86 and at least partially into the branch vessel 84.

In a follow-up step, after the balloons 24, 26 have been deflated and the catheter branches 12, 14 removed, a separate balloon member can be advanced through the lateral branch opening to treat the branch vessel 84 and further open the expandable structure 55 into the branch vessel 84. In a still further step, an additional branch stent can be advanced through the lateral branch opening 55 and into the branch vessel 84 for treatment of the branch vessel 84.

The particular method steps described above can be altered in other example treatment methods. For example, one of the guidewires 60, 62 can be advanced with the catheter assembly 10 to the vessel bifurcation. In another example, the balloons 24, 26 can be inflated sequentially rather than simultaneously for purposes of, for example, improving alignment of the lateral branch opening 55 with the ostium into the branch vessel.

The catheter assembly 10 can include marker material that is visible under X-ray or in fluoroscopy procedures. FIG. 6 illustrates markers 1-4 positioned along the distal end portions of the main and side catheter branches 12, 14. Any features of the system 10 that include marker material can be more easily identified and distinguished under X-ray or in fluoroscopy procedures. Some example marker materials include gold, platinum and tungsten. In one embodiment, the marker material can be included in a band structure that is secured to at least one of the main and side catheter branches 12, 14. In other embodiments, the marker material is part of the material composition of portions of the main and side catheter branches 12, 14. Viewability of features of the catheter assembly 10 under X-ray or fluoroscopy can assist the physician operating the system 10 to more easily adjust a position of the system 10 relative to the vessel bifurcation 80. Example markers and marker materials suitable for use with system 10 are described in U.S. Pat. No. 6,692,483 to Vardi, et al, and co-pending U.S. Patent Publication No. 2007/0203562-A1, titled MARKER ARRANGEMENT FOR BIFURCATION CATHETER, which patent matters are incorporated herein by reference.

A wide variety of stents, catheters, and guidewire configurations can be used with the catheter assembly embodiments of the present disclosure. The inventive principles disclosed herein should not be limited to any particular design or configuration. Some example stents that can be used with the catheter assemblies disclosed herein can be found in, for example, U.S. Pat. Nos. 6,210,429, 6,325,826, 6,706,062, and 7,220,275, and U.S. Published Patent Application No. 2004/0176837 titled SELF-EXPANDING STENT AND CATHETER ASSEMBLY AND METHOD FOR TREATING BIFURCATIONS, the entire contents of which are incorporated herein by reference. In general, the aforementioned stents include a lateral branch opening located between distal and proximal open ends of the stent. The lateral branch opening defines a path between an inner lumen of the stent and an area outside of the stent. The stent lateral branch opening is distinct from the cell openings defined between strut structures from which the stent sidewall is constructed. In some stents, the lateral branch opening can be surrounded by expandable structure. The expandable structure can be configured to extend radially into the branch lumen of the bifurcation upon expansion of, for example, an inflatable portion of the bifurcation treatment system. Typically, the stent is expanded after being positioned in the main lumen with the lateral branch opening aligned with an opening into the branch lumen. Alignment of the lateral branch opening with the opening into the branch lumen includes both radial and axial alignment. The stent, including the expandable structure surrounding the lateral branch opening, can be expanded with a single expansion or multiple expansions using one or more inflatable members.

The main and side balloons, and all other balloons disclosed herein, can be made of any suitable balloon material including compliant and non-compliant materials and combinations thereof. Some example materials for the balloons and catheters disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/ polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid®L21011F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory® (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid® (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL® or HYTREL®, or polyethylene terephthalate (PET) and a thermoplastic elastomer, such as a PBT thermoplastic elastomer. Additional examples of balloon material can be found in U.S. Pat. No. 6,146,356, which is incorporated herein by reference.

VI. Conclusion

One aspect of the present disclosure relates to catheter assembly that includes a main catheter branch and a side catheter branch. The main catheter branch includes a catheter shaft, a main balloon, and a side balloon. The catheter shaft has a proximal end portion and a distal end portion, wherein the distal end portion defines a main inflation member. The main balloon has a distal waist at a distal end portion thereof and a proximal waist portion at a proximal end portion thereof. The side balloon has an inflatable portion, a distal waist at a distal end portion thereof, and a proximal waist portion at a proximal end portion thereof. The side balloon is configured to extend in a radial direction relative to the main balloon when the side balloon is inflated, the inflatable portion positioned at a location between the proximal and distal end portions of the main balloon, the proximal waist of the side balloon and the proximal waist of the main balloon operatively mounted in fluid communication to the main inflation lumen shaft at a proximal balloon joint positioned at the distal end portion of the catheter shaft.

Another aspect of the present disclosure relates to a catheter assembly that includes a main catheter branch, a side catheter branch, and a stent. The main catheter branch has a proximal end portion and a distal end portion. The distal end portion includes a catheter shaft, a main guidewire housing, and a main balloon. The catheter shaft has a distal end portion and defines a main inflation lumen. The main guidewire housing extends distally beyond the distal end portion of the catheter shaft and defines a main guidewire lumen. The main balloon has a proximal waist portion and a distal waist portion. The side balloon has an inflatable portion, a proximal waist portion, and a distal waist portion. The proximal and distal waist portions of the side balloon define a side inflation lumen, and the proximal waist portion of the side balloon and the proximal waist portion of the main balloon are operably mounted in fluid communication with the main inflation lumen at a proximal balloon joint. The side catheter branch has a distal end portion, and the side catheter branch defines a side guidewire lumen. The stent has proximal and distal open ends and a lateral branch opening defined in the stent at a location between the proximal and distal open ends. The distal end portion of the side catheter branch extends through the lateral branch opening prior to inflation of the main balloon and the side balloon.

A further aspect of the present disclosure relates to a method of manufacturing a catheter assembly. The catheter assembly includes a main catheter branch having a catheter shaft, a main balloon, and a side balloon. The catheter shaft has a distal end portion and defines a main inflation lumen. The main balloon has a proximal waist at a proximal end portion thereof and a distal waist at a distal end portion thereof. The side balloon has an inflatable portion and a proximal waist portion extending proximally from the inflatable portion. The inflatable portion is positioned at a location between the proximal and distal waists of the main balloon. The inflatable portion extends radially relative to the main balloon when the side balloon is inflated. The method includes positioning a proximal open end of the side balloon proximal waist and a proximal open end of the main balloon proximal waist adjacent to each other and in fluid communication with the main inflation lumen at the distal end portion of the catheter shaft, and securing the side balloon proximal waist, the main balloon proximal waist, and the distal end portion of the catheter shaft together a proximal balloon joint while maintaining fluid communication between the side balloon proximal waist, the main balloon proximal waist, and the main inflation lumen.

It is noted that not all of the features characterized herein need to be incorporated within a given arrangement, for the arrangement to include improvements according to the present disclosure.

The invention claimed is:

1. A method of manufacturing a catheter assembly, the catheter assembly including a main catheter branch having a catheter shaft, a main balloon, and a side balloon, the catheter shaft having a distal end portion and defining a main inflation lumen, the main balloon having a proximal waist at a proximal end portion thereof and a distal waist at a distal end portion thereof, the side balloon having an inflatable portion and a proximal waist portion extending proximally from the inflatable portion, the inflatable portion positioned at a location between the proximal and distal waists of the main balloon, the inflatable portion extending radially relative to the main balloon when the side balloon is inflated, the method comprising:
   (a) positioning a proximal open end of the side balloon proximal waist and a proximal open end of the main balloon proximal waist with outer surfaces adjacent to each other and in fluid communication with the main inflation lumen at the distal end portion of the catheter shaft; and
   (b) simultaneously securing the side balloon proximal waist, the main balloon proximal waist, and the distal end portion of the catheter shaft together at a single proximal balloon joint while maintaining fluid communication between the side balloon proximal waist, the main balloon proximal waist, and the main inflation lumen.

2. The method of claim 1, further comprising (c) before the securing step, inserting a first mandrel into the distal end portion of the catheter shaft and into the main balloon through the proximal waist of the main balloon, and inserting a second mandrel into the distal end portion of the catheter shaft and into the proximal waist of the side balloon.

3. The method of claim 2, wherein the securing step includes applying heat to create a heat bond between the side balloon proximal waist, the main balloon proximal waist, and the distal end portion of the catheter shaft, permitting the proximal balloon joint to cool, and removing the mandrels.

4. The method of claim 3, wherein heat is applied with a laser.

5. The method of claim 1, wherein the step of securing includes applying heat to create a heat bond between the side balloon proximal waist, the main balloon proximal waist, and the distal end portion of the catheter shaft.

6. The method of claim 1, wherein the securing step includes applying an adhesive and curing the adhesive.

* * * * *